United States Patent
Ding et al.

(10) Patent No.: US 7,517,694 B2
(45) Date of Patent: Apr. 14, 2009

(54) METERING TIP WITH INTERNAL FEATURES TO CONTROL FLUID MENISCUS AND OSCILLATION

(75) Inventors: Zhong Ding, Fairport, NY (US); Merrit N. Jacobs, Fairport, NY (US); James D. Shaw, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 489 days.

(21) Appl. No.: 10/626,259

(22) Filed: Jul. 24, 2003

(65) Prior Publication Data

US 2004/0072367 A1  Apr. 15, 2004

Related U.S. Application Data

(60) Provisional application No. 60/398,918, filed on Jul. 26, 2002.

(51) Int. Cl.
*G01N 21/17* (2006.01)
*G01N 21/62* (2006.01)
*G01N 1/00* (2006.01)

(52) U.S. Cl. ............ 436/165; 436/164; 436/171; 436/172; 436/180

(58) Field of Classification Search ........ 422/99–100; 436/164–165, 171–172, 180
See application file for complete search history.

(56) References Cited

U.S. PATENT DOCUMENTS

| | | | |
|---|---|---|---|
| 3,449,081 A | 6/1969 | Hughes | |
| 3,780,935 A * | 12/1973 | Lukacs et al. | 494/37 |
| 4,212,204 A * | 7/1980 | St. Amand | 73/864.11 |
| 4,347,875 A * | 9/1982 | Columbus | 422/100 |
| 4,398,382 A * | 8/1983 | Suovaniemi et al. | 53/431 |
| 4,961,350 A | 10/1990 | Tennstedt | |
| 5,073,347 A * | 12/1991 | Garren et al. | 422/100 |
| 5,200,151 A * | 4/1993 | Long | 422/100 |
| 5,223,225 A * | 6/1993 | Gautsch | 422/100 |
| 5,364,595 A * | 11/1994 | Smith | 422/100 |
| 5,827,745 A * | 10/1998 | Astle | 436/54 |
| 5,844,686 A | 12/1998 | Treptow et al. | |
| 6,123,905 A * | 9/2000 | Torti et al. | 422/100 |
| 6,174,733 B1 * | 1/2001 | Chen | 436/501 |
| 6,516,977 B2 * | 2/2003 | Chan | 222/394 |
| 6,596,240 B2 * | 7/2003 | Taggart et al. | 422/100 |
| 6,641,993 B1 * | 11/2003 | Jacobs et al. | 435/4 |
| 6,921,513 B2 * | 7/2005 | Schubert et al. | 422/100 |
| 6,967,004 B2 * | 11/2005 | Rainin et al. | 422/100 |
| 7,033,543 B1 * | 4/2006 | Panzer et al. | 422/100 |
| 2002/0037239 A1 * | 3/2002 | Komatsu | 422/100 |
| 2003/0039589 A1 * | 2/2003 | Smith | 422/100 |
| 2003/0082078 A1 * | 5/2003 | Rainin et al. | 422/100 |
| 2003/0129094 A1 * | 7/2003 | Schubert et al. | 422/100 |
| 2003/0165408 A1 * | 9/2003 | Takeda et al. | 422/100 |
| 2005/0181519 A1 * | 8/2005 | Karg et al. | 436/180 |
| 2005/0255005 A1 * | 11/2005 | Motadel | 422/100 |

* cited by examiner

*Primary Examiner*—Brian R. Gordon
(74) *Attorney, Agent, or Firm*—Hiscock & Barclay, LLP

(57) ABSTRACT

A metering tip for use in a clinical analytical apparatus includes a tapered body having at least one interior stepped areas. Each of the stepped areas include a sharp diametrical edge for latching a fluid meniscus being dispensed from the tip and for reducing fluid oscillation during metering.

1 Claim, 3 Drawing Sheets

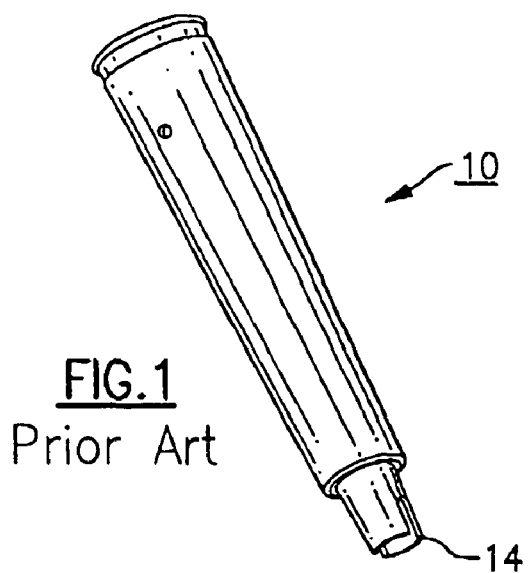
FIG.1
Prior Art
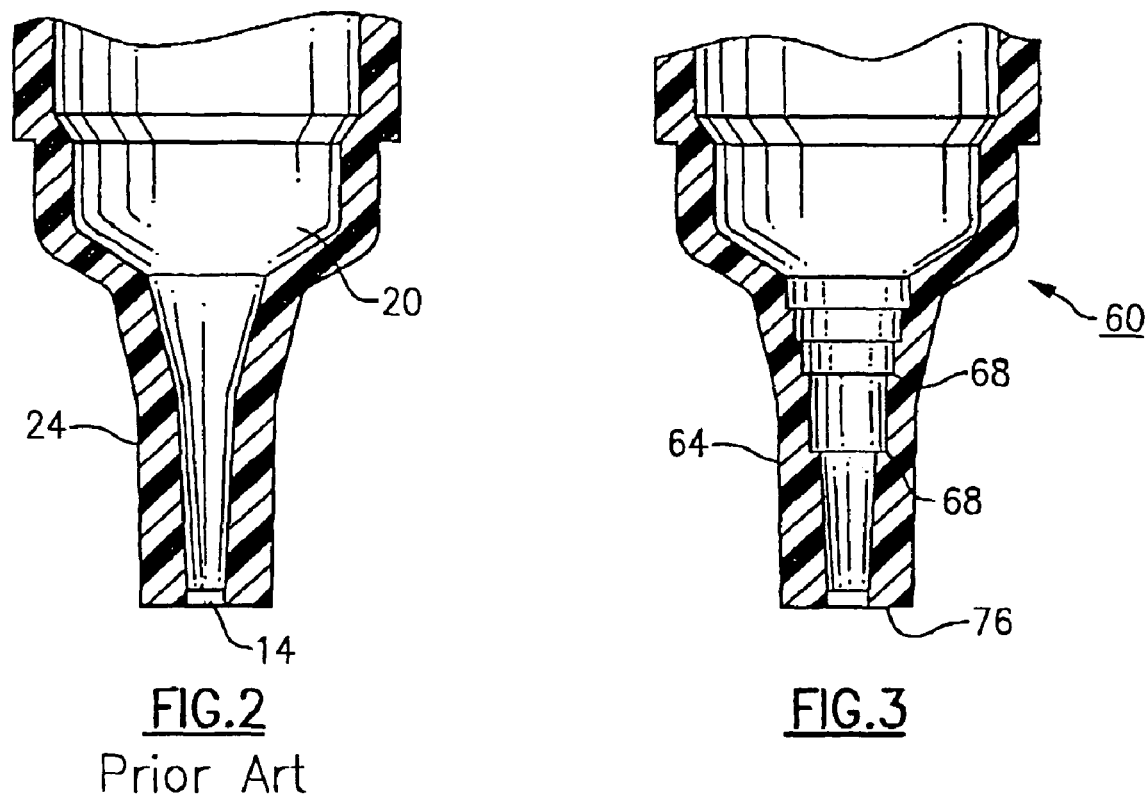
FIG.2
Prior Art
FIG.3

METERING TIP WITH INTERNAL FEATURES TO CONTROL FLUID MENISCUS AND OSCILLATION

CROSS REFERENCE TO RELATED APPLICATION

This application claims priority under 35 USC 119(e) upon provisional Patent Application No. 60/398,918, filed Jul. 26, 2002 and entitled: Metering Tip With Internal Features To Control Fluid Meniscus and Oscillation, the entire contents of which are incorporated herein by reference.

FIELD OF THE INVENTION

This invention relates generally to an improved metering tip which includes at least one stepped area formed on the interior of the tip that more effectively control fluid flow therefrom.

BACKGROUND OF THE INVENTION

In automated clinical apparatus used in the analysis of blood, sera and body fluids, such as those manufactured by Abbott Laboratories and Ortho Clinical Diagnostics, Inc., among others, it is common place to aspirate a quantity of fluid sample or reagent into a disposable, usually plastic metering tip. The tip transports fluid to another location within the analyzer and then subsequently dispenses the fluid into a reaction vessel such as a cuvette, for subsequent incubation and analysis. Such metering tips are typically cylindrically shaped with a narrowed nozzle at the bottom end thereof, the design being essentially unchanged from tips commonly used on hand-held pipettes. Advancing analyzer technology has moved toward higher speed and more sensitive monitoring of metering events. Other advances require functions beyond simple aspirating and dispensing of fluids. To that end, traditional tip designs are no longer adequate.

After aspiration of fluid into the metering tip and for the remaining steps of a typical metering cycle, fluid is supported in the tip by a After aspiration of fluid into the metering tip and for the remaining steps of a typical metering cycle, fluid is supported in the tip by a combination of forces that counteract the weight of the fluid column. These forces include the following:

i) a slight vacuum that is supplied by the metering system;
ii) surface tension effects of the upper fluid meniscus acting on the internal bore of the tip; and
iii) surface tension effects of the lower fluid meniscus acting on the nozzle of the tip.

The interaction between the fluid meniscus and the nozzle of the tip is a significant portion of the above-noted force balance. The intersection of the bore of the tip with the end of the tip (subsequently referred to as the tip "land") usually consists of a sharp edge, as does the intersection of the land of the tip with the external nozzle. This geometry is more than merely a convenience to the overall manufacturing process. Surface tension of the fluid interacting with sharp edges of the tip land form resistive energy barriers to fluid meniscus movement. It has been learned that these sharp-edged features of the tip nozzle effectively "latch" the meniscus at either the bore edge or the external nozzle edge of the tip land. Ideally, this "latching" of the fluid meniscus is sufficient to keep the fluid in place in spite of changes in pressure within the metering system and acceleration forces due to transporting the tip within the various stations of the clinical analyzer.

Due to demands for higher throughput of automated analyzers, metering systems need to function at high speeds. This is difficult, in that most metering systems employing disposable tips as metering elements utilize air as the working fluid. Since air is compressible, when the fluid in the tip is accelerated in the vertical direction, forces may be sufficient to break the meniscus "latching" force, causing the fluid column to begin oscillating within the confines of the tip. Once the "latch" has been broken, it is difficult to re-establish, even in the case of analyzer metering systems that have active monitoring and control of internal pressure. Such oscillations can be extremely problematic for a number of reasons. First, and in the case of an analyzer system that dispenses sample onto a dry reagent, having fluid touch the reagent prior to actual fluid dispense can bias the assay result. Second, analyzers having software for detecting the presence of an air bubble in the dispensed volume may experience an increased frequency of errors if the oscillation of fluid in the tip results in the lower fluid meniscus moving up into the barrel of the tip. Third, extreme fluid oscillation can result in loss of fluid from the tip, reducing the volume that is subsequently dispensed into the reaction vessel. In typical automated analyzers, the fluid dispensed is a relatively small volume and must be held to precise tolerances to achieve the needed precision from the analytical result. The loss of even a small amount of sample can bias that assay result.

Given the severity of problems, such as those noted above that are caused by fluid oscillation, it would be useful to have a metering tip that provided features to damper or effectively reduce and/or minimize oscillation.

SUMMARY OF THE INVENTION

It is a primary object of the present invention to avoid the above-noted deficiencies of the prior art.

It is another primary object of the present invention to reduce the occurrence of fluid oscillations in a dispensed or metered liquid within the confines of a metering tip.

Therefore and according to a preferred aspect of the invention, there is provided a metering tip that includes a tapered dispense end and an interior for retaining a fluid, said metering tip having a plurality of stepped areas within said interior, each of said stepped areas including a sharp diametrical edge for latching a fluid meniscus and for reducing oscillation of a dispensed fluid.

Preferably, a series of adjacent stepped areas are provided within the tip interior to significantly reduce or prevent fluid oscillation effects, in which each of the stepped areas preferably have a sharp diametrical edge for latching a dispensed fluid meniscus.

According to one embodiment, the metering tip further includes a read area that permits optical or other examination of a contained fluid. According to a preferred embodiment, at least one stepped area is provided in relation to the read area of the metering tip to permit examination of a minimized fluid dead volume remaining in the tip.

An advantage achieved by the present invention is that the inclusion of at least one stepped area in a metering tip will significantly reduce fluid oscillation effects.

Another advantage is that providing a stepped area relative to the read window of the tip permits optical tests, such as spectrophotometer readings, to be reliably performed using a minimized dead volume in the tip.

These and other objects, features and advantages will become readily apparent from the following Detailed Description which should be read in conjunction with the accompanying drawings.

BRIEF DESCRIPTION OF THE DRAWINGS

FIG. 1 is a side perspective view of a metering tip made in accordance with the prior art;

FIG. 2 is a sectional view of the metering tip of FIG. 1;

FIG. 3 is a sectional view of a metering tip made in accordance with the present invention;

DETAILED DESCRIPTION

Figure 4:
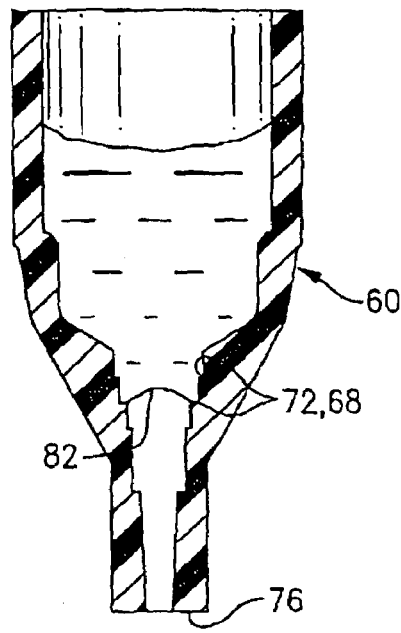
FIGS. 4-10 are sectional views of the metering tip of FIG. 3 illustrating a time-phased sequence of fluid dispensing.
Figure 5:
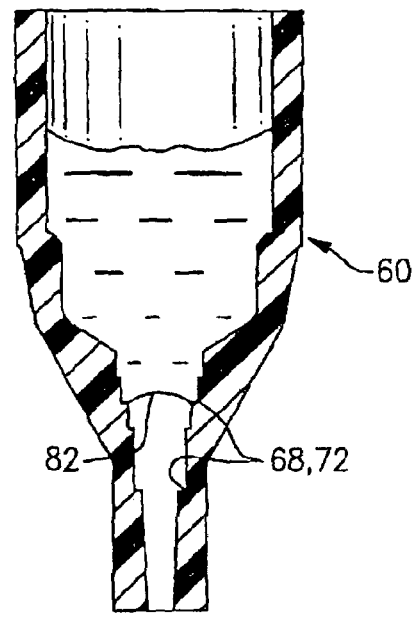
Figure 6:
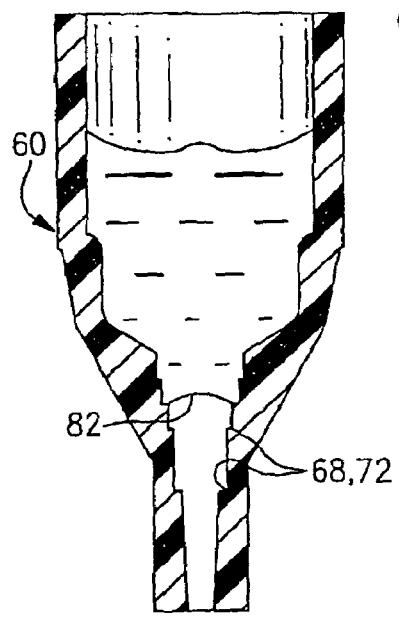
Figure 7:
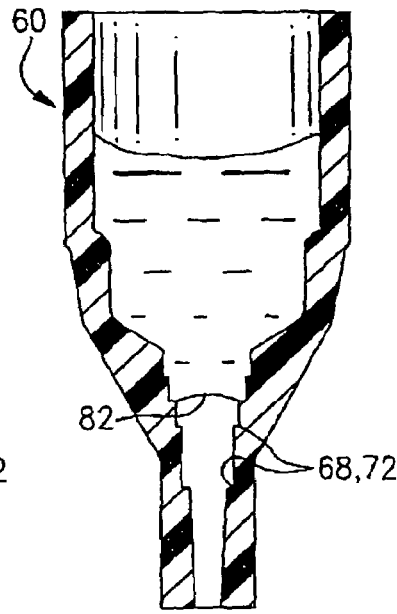
Figure 8:
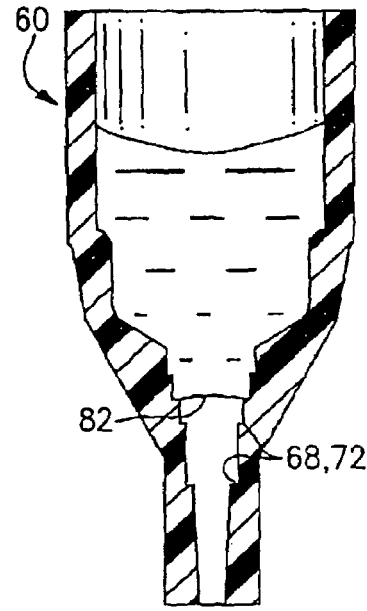
Figure 9:
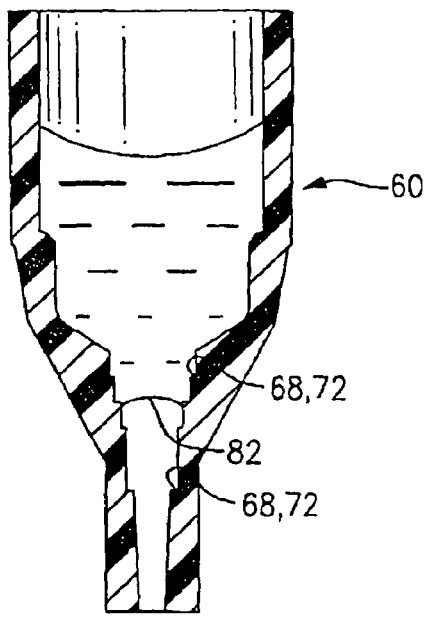
Figure 10:
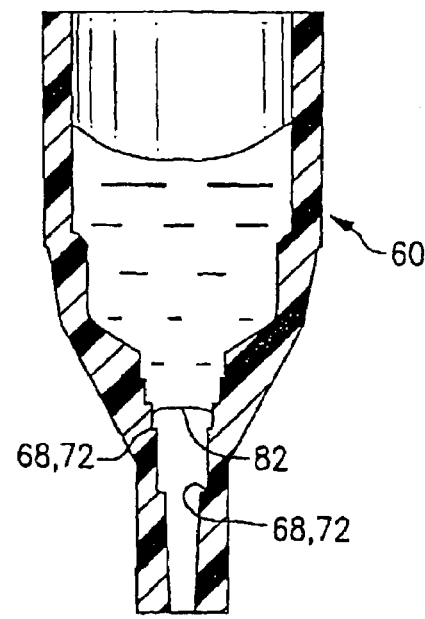

The present invention describes certain embodiments of a metering tip used primarily in clinical analyzers for aspirating and dispensing fluids. It should be readily evident, however, that other designs utilizing the inventive concepts described herein could easily be imagined by one of suitable skill in the field.

The present tip design effectively reduces fluid oscillation in cases in which the lower fluid meniscus becomes "unlatched" from the tip land. For background purposes, FIGS. 1 and 2 depict a known metering tip 10. The tip 10 is made preferably from a molded plastic material and is defined by a tapered cylindrical construction including a lower tip opening 14, a tip nozzle 24, and an upper tip opening 18, the tip being defined by a hollow tapered interior 20. As shown in FIG. 2, the internal shape of the metering tip 10 includes a continuous or smooth transition between each of its tapered surfaces and this design typically common to the majority of metering tips used in both automated analyzers as well as pipette tips.

FIG. 3 depicts a metering tip 60 that is made in accordance with a preferred embodiment of the present invention. The tip 60 includes an internal nozzle 64 having a plurality of adjacent interior stepped areas 68. Each of the plurality of adjacent stepped areas 68 include a sharp interior diametrical edge 72 that provides similar interaction with a fluid meniscus as does the sharp edges of the tip land 76. Therefore, and as a fluid meniscus 82 moves past each diametrical edge 72 of a stepped area 68, as shown in the time-phased drawings depicted in FIGS. 4-10, the fluid meniscus will attempt to "latch" on that edge, thereby slowing the movement. Providing a series of stepped areas 68 within the tip 60 as in the present embodiment extends this damping behavior over a greater length of the tip nozzle 64 in order to damp out more intense oscillations, as shown in FIGS. 4-10.

Tips of configurations shown in FIG. 3 have been tested, for comparative purposes, on current analyzer platforms. This testing shows that fluid oscillation and any associated metering errors are substantially minimized by the inclusion of adjacent stepped areas 68 in the interior of the tip 60.

The herein described metering tip 60 of FIG. 3, including the plurality of oscillation damping stepped areas 68, performs an additional function. In this other application, after all the samples have been dispensed from the metering tip 60, it is often desired to take a spectrophotometric read of the fluid remaining in the tip (this remaining fluid is subsequently referred to throughout as "dead volume").

Figure 12:
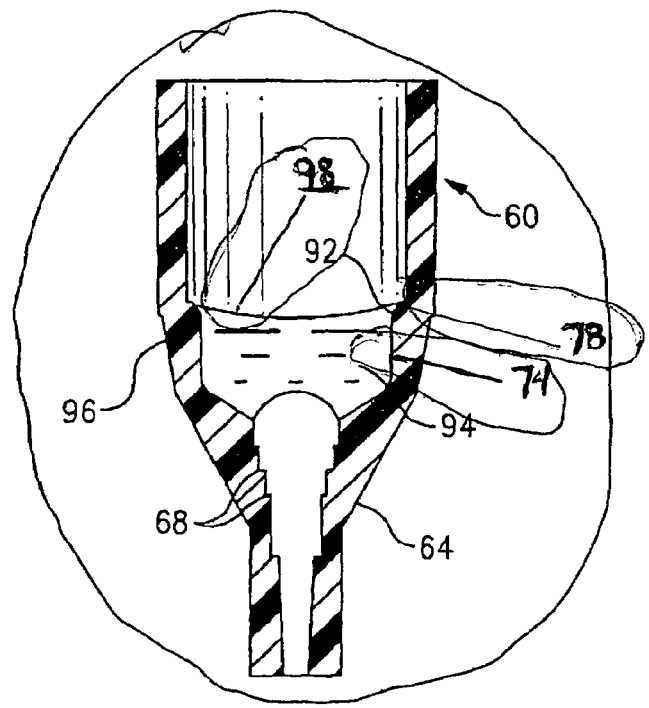
FIG. 12 illustrates the creation of a dead fluid volume for optical read purposes in a metering tip made in accordance with the present invention.

Referring to FIG. 12, a spectrophotometric read is taken through a read window 96 located in a cylindrical portion 74 of the tip 60 immediately below another defined stepped area 78 and above the external cone. Since timing constraints make it impractical to perform this spectrophotometric read through the tip 60 while it is still attached to a metering system probe (not shown), it is desirable to remove the tip 60 from the metering system, store the tip and perform the spectrophotometric read at a later time. Removing the tip 60 with the nozzle 64 open to air would likely cause loss of the fluid or dispersal of the fluid within the tip. Were this to occur, fluid would not be properly positioned for the spectrophotometric read. One effective solution to this problem is to seal the tip 60 by contacting the tip to a heated anvil (not shown), melting the end of the tip nozzle. The sealed tip effectively becomes a "cuvette" which can be stored in a storage device (not shown) for a later spectrophotometric read. Additional details relating to the above sealing technique are described in copending commonly owned U.S. Ser. No. 09/910,399, the entire contents of which are herein incorporated by reference.

Referring to FIG. 12 and prior to sealing, the dead volume 94 of fluid is first drawn up into the nozzle 64 of the metering tip 60. This drawing step is done for two reasons. Firstly, the air bubble that is created at the end of the tip nozzle 64 insulates the retained fluid from the heat of the sealing operation. Heat can effect the concentration of some analytes. Secondly, it is highly desirable to minimize the dead volume, especially when the fluid is a pediatric sample.

Figure 11:
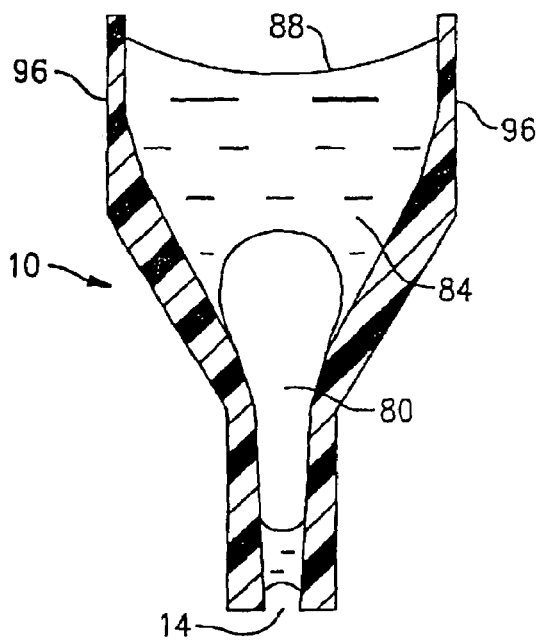
FIG. 11 illustrates the creation of a dead fluid volume for optical read purposes in a prior art metering tip.

As shown in FIG. 12, the aspirated air bubble elevates the upper meniscus 98 of the dead volume 94 so that there are no optical effects due to the upper meniscus during the spectrophotometric read. A comparison of this prior art effect is shown in FIG. 11. As previously noted, the plurality of steps inside the tip nozzle 64 have the effect of "latching" the bubble in place to withstand the shock of tip ejection and transport in the storage device (not shown) prior to the spectrophotometric read.

Still referring to FIG. 12, and to further reduce the optical effect of the upper meniscus, another internal stepped area 92 is added within the tip 60 just above the spectrophotometric read area window 96. Without this stepped area 92 and referring to the prior art nozzle depicted in FIG. 11, the upper meniscus 88 would assume an approximately spherical curvature depending on surface tension. At the low end of tolerance of dead volume, the curvature could cause optical reflection, thereby effecting the spectrophotometric read accuracy. Also, due to the shock of tip ejection and subsequent transport in the storage device (not shown), the upper meniscus 88 could tilt so that the low side of the meniscus could extend well into the optical path of the spectrophotometer. The effect of the stepped area 92 is to effectively "latch" and thereby flatten the meniscus 88.

While the present invention has been particularly shown and described with reference to the preferred mode as illustrated in the drawings, it will be understood by one skilled in the art that various changes in detail may be effected therein without departing from the spirit and scope of the invention as defined by the claims.

PARTS LIST FOR FIGS. 1-12

10 metering tip
14 tip opening, lower
18 tip opening, upper
20 interior
24 tip nozzle
60 metering tip
64 internal nozzle
68 stepped areas
72 diametrical edges
74 cylindrical portion 76 tip land
78 external stepped area
80 air bubble
82 meniscus
84 dead volume
88 meniscus, fluid
92 internal stepped area
94 dead volume
96 read window
98 meniscus, fluid

We claim:

1. A method for performing an optical read of dead volume of fluid in a metering tip, said tip containing a volume of aspirated fluid, a portion of said fluid being dispensed as samples, said tip comprising at least one stepped area within an interior of said tip, said at least one stepped area including a sharp diametrical edge, said method including the steps of:

i) dispensing samples from the volume of aspirated fluid from said metering tip through a lower tip opening;

ii) aspirating an air bubble into said tip, thereby drawing the remaining fluid retained in said metering tip upwardly and into a cylindrical section of said metering tip, said cylindrical portion being defined with a substantially constant planar internal diameter defining a read window wherein said at least one stepped area is located above said read window, wherein said stepped area flattens the upper meniscus of said retained volume of fluid;

iii) sealing the lower tip opening of said metering tip; and iv) optically reading the retained volume through said defined read window.

* * * * *